United States Patent [19]
Northcutt

[11] Patent Number: 5,997,469
[45] Date of Patent: Dec. 7, 1999

[54] SEXUAL AID DEVICE

[76] Inventor: Michael E. Northcutt, 470 E. Calaveras Blvd., Ste D-200, Milpitas, Calif. 95035

[21] Appl. No.: 09/027,351

[22] Filed: Feb. 21, 1998

[51] Int. Cl.⁶ .................................................. A61F 5/00
[52] U.S. Cl. ................................. 600/38; 600/41
[58] Field of Search ................... 600/38, 39, 41; 128/842, 844, 845, 883

[56] References Cited

U.S. PATENT DOCUMENTS

| | | | |
|---|---|---|---|
| 2,024,983 | 12/1935 | Street | 600/38 |
| 3,461,863 | 8/1969 | Sullinger | 600/41 |
| 4,203,432 | 5/1980 | Koch | 600/41 |
| 4,960,113 | 10/1990 | Seeberg-Elverfeldt | 600/38 |
| 5,647,837 | 7/1997 | McCarty | 600/38 |
| 5,810,710 | 9/1998 | Burgos | 600/38 |

FOREIGN PATENT DOCUMENTS

| | | | |
|---|---|---|---|
| 000440947 | 2/1927 | Germany | 600/41 |
| 000734394 | 7/1955 | United Kingdom | 600/41 |

*Primary Examiner*—John P. Lacyk
*Attorney, Agent, or Firm*—The Kline Law Firm

[57] ABSTRACT

A sexual aid device that encircles the base of the penis. The device may be constructed as a single ring, or as a set of rings that can be used together in various conformations. The device includes a size adjustment means that allows the user to vary the size of the central through hole so that a user of the device is always ensured of a proper fit. The device may also include an extension means to directly stimulate the female's clitoral region. Alternatively, the device may be formed with an oval shape as opposed to a round shape to achieve the objective of direct stimulation of the clitoris.

16 Claims, 14 Drawing Sheets

5,997,469

SEXUAL AID DEVICE

FIELD OF THE INVENTION

The present invention relates generally to sexual aids, and more particularly is a device that increases sexual pleasure when used during intercourse.

BACKGROUND OF THE INVENTION

Inasmuch as a healthy sexual relationship is vital to most marriages and to physical personal relationships, there has through the course of time been a great deal of interest in the area of sexual compatibility devices. Many devices have been created to either heighten couples' sexual pleasure or to aid in overcoming problems of impotency.

Due to the physiology involved, nearly all such devices are constructed so as to fit around the male's penis. In order to remain in place during the sexual act, the device must fit snugly on the male member. However, one simple fact of life is that not all male sexual organs are the same size. But due to the psychological implications inherent in size of sex organ, no prior art sexual aid devices are constructed to fit men of differing sizes. Because of this limitation, the prior art devices have not been commercial successes.

Accordingly, it is an object of the present invention to provide a sexual aid device that accommodates sexual organs of different sizes.

It is a further object of the present invention to provide a device that is variable in the extent of penetration of the woman.

It is a still further object of the present invention to provide a modular device that can be assembled according to the preference of the user.

SUMMARY OF THE INVENTION

The present invention is a sexual aid device that encircles the base of the penis. The device may be constructed as a single ring, or as a set of rings that can be used together in various conformations. The device includes a size adjustment means that allows the user to vary the size of the central through hole so that a user of the device is always ensured of a proper fit. The device may also include an extension means to directly stimulate the female's clitoral region. Alternatively, the device may be formed with an oval shape as opposed to a round shape to achieve the objective of direct stimulation of the clitoris.

An advantage of the present invention is that the size adjustment means allows a user to always obtain a proper fit.

Another advantage of the present invention is that the modular aspects of the device allow a user to vary the penetration characteristics of the device.

These and other objects and advantages of the present invention will become apparent to those skilled in the art in view of the description of the best presently known mode of carrying out the invention as described herein and as illustrated in the drawings.

DETAILED DESCRIPTION OF THE INVENTION

The present invention is a sexual aid device that is adapted to encircle the base of a user's penis. The device may be constructed as a single ring, or as a set of rings that can be used together in various conformations. The device generally includes a size adjustment means of some type that allows the user to vary the size of the central through hole. This ensures that a user of the device is always ensured of a proper fit.

Figure 1:
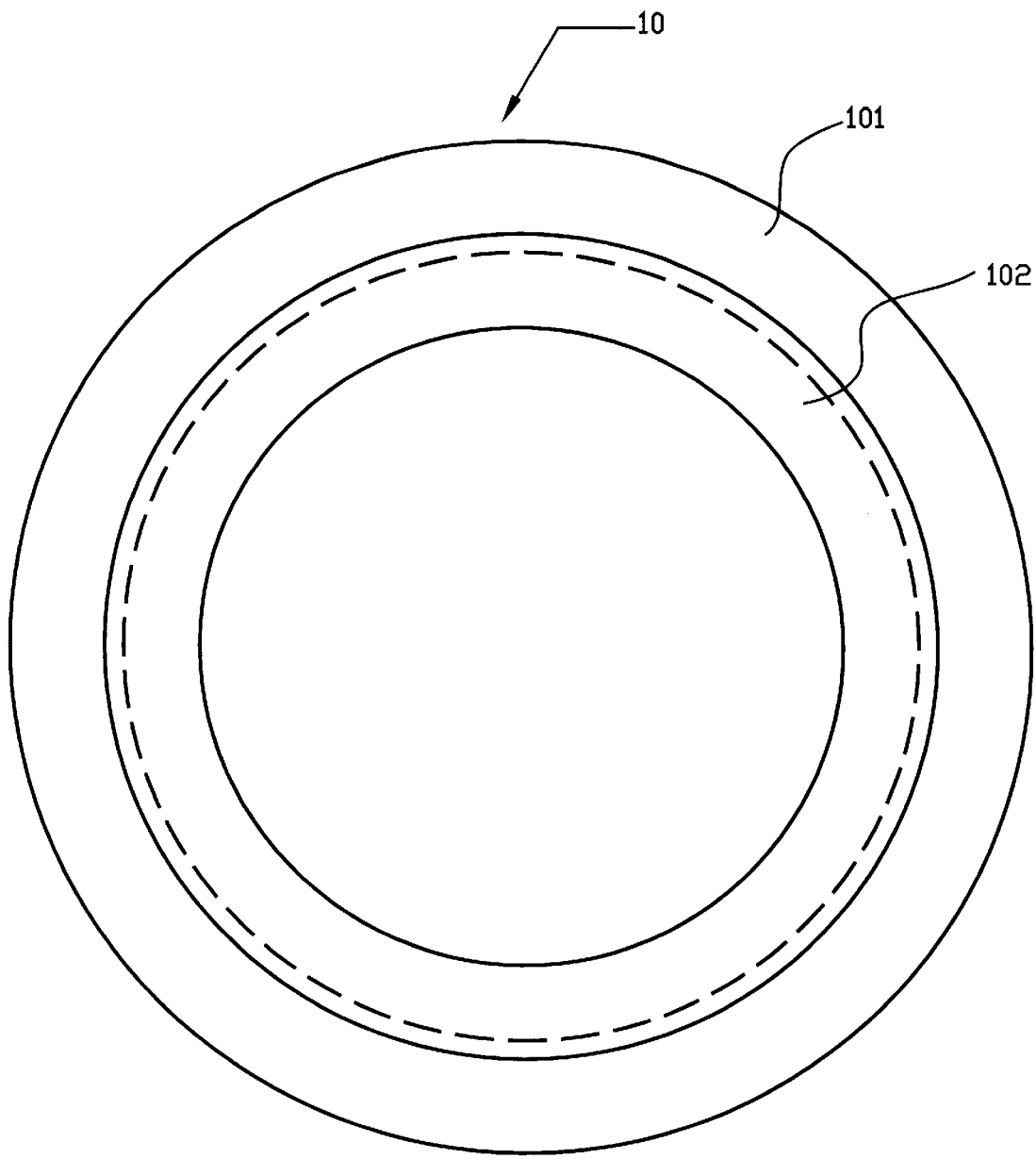
FIG. 1 is a top view of the preferred embodiment of the sexual aid device of the present invention.
Figure 2:
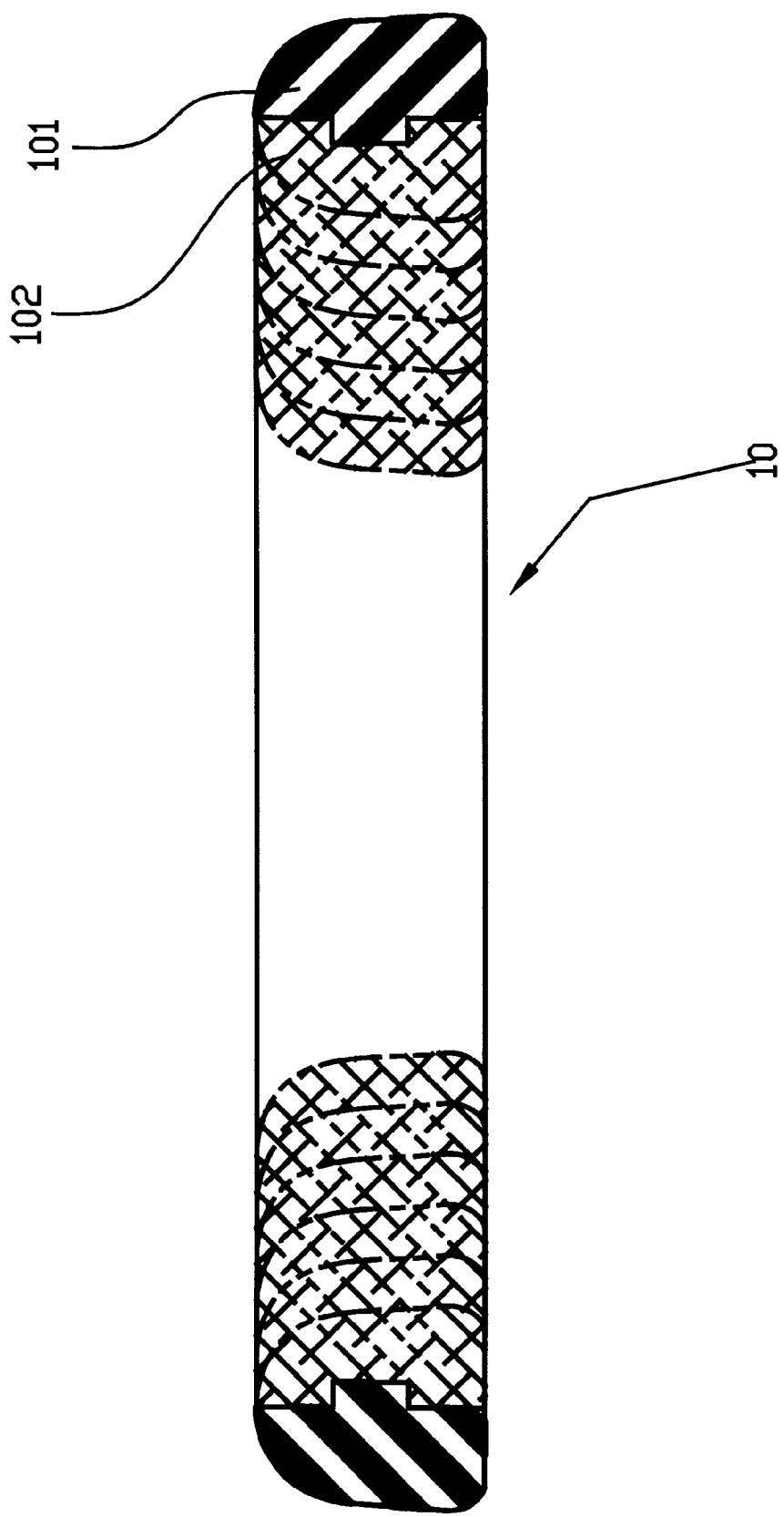
FIG. 2 is a cross section of the device of the present invention.

In a first preferred embodiment shown in FIGS. 1 and 2, the device includes a main body 10 with a central through hole 11. The main body 10 is comprised of an outer ring 101 that interlocks with an inner ring 102. The size adjustment means for the embodiment illustrated in these figures is the inner ring 102. The size of the central through hole is adjusted by varying the size of the inner ring 102.

Figure 3:
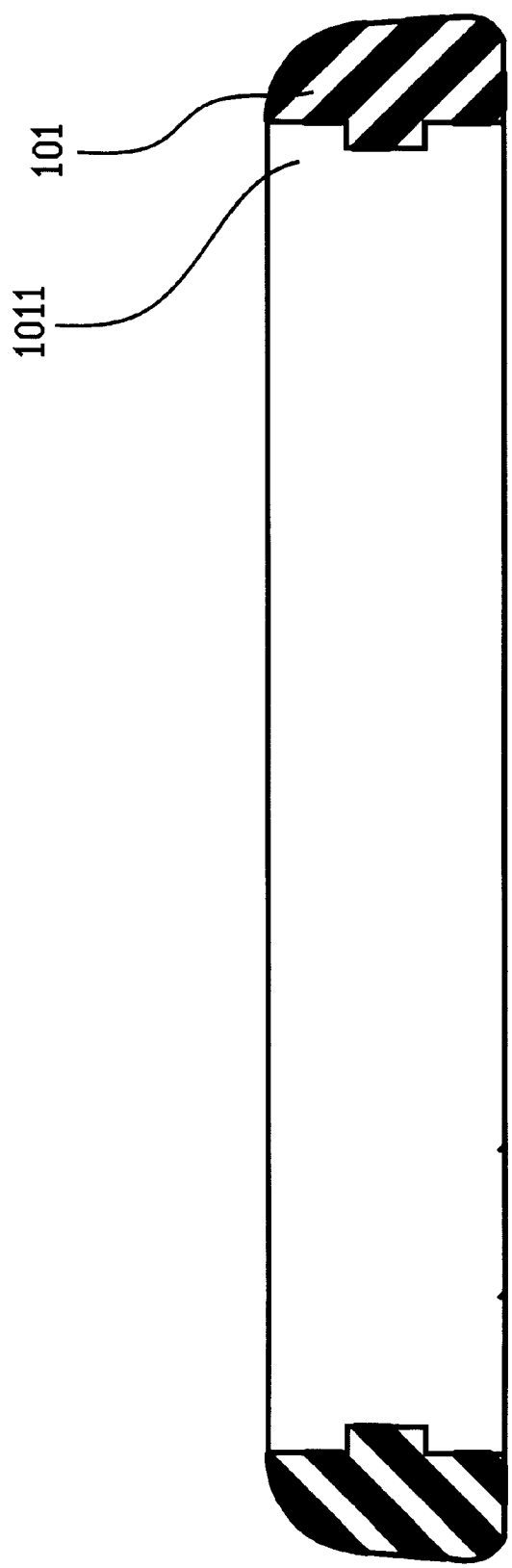
FIG. 3 is a cross section of the outer ring of the present invention.
Figure 4:
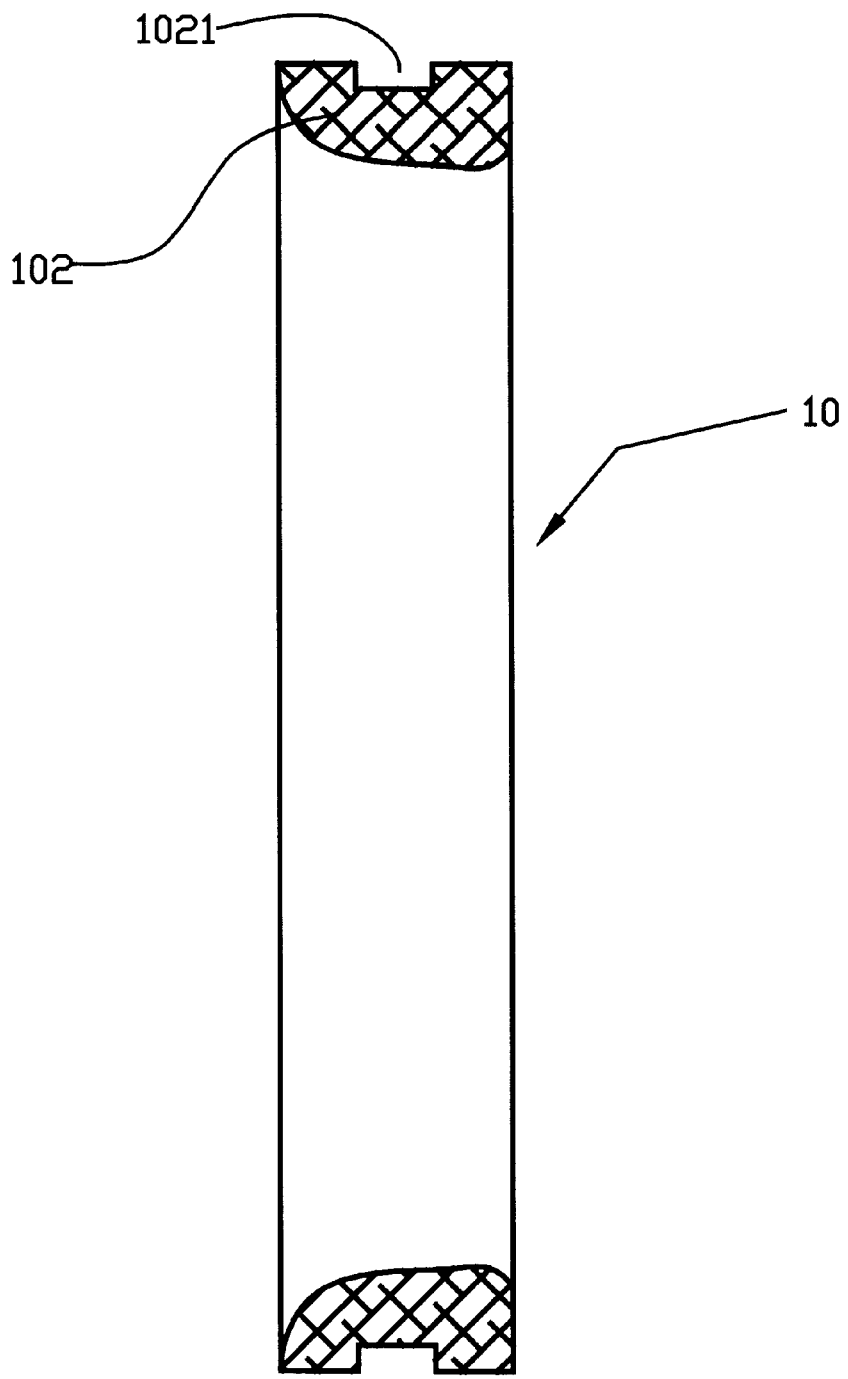
FIG. 4 is a cross section of the inner ring of the present invention.

The outer ring 101 (detail shown in FIG. 3) includes an annular projecting ridge 1011. The inner ring 102 (detail shown in FIG. 4) includes an annular slot 1021 that receives the annular ridge 1011. The meshing of the annular ridge 1011 and the annular slot 1021 ensures that the outer ring 101 and the inner ring 102 are securely joined together.

It is envisioned that in practice, the device will be provided with a single outer ring 101 and a plurality of inner rings 102 of varying widths. The user will select which of the inner rings 102 provides him with the proper fit, and insert the selected inner ring 102 into the outer ring 101. The user is thus assured of an appropriate fit without the uncomfortable requirement of choosing a size at the point of sale of the device.

Figure 5:
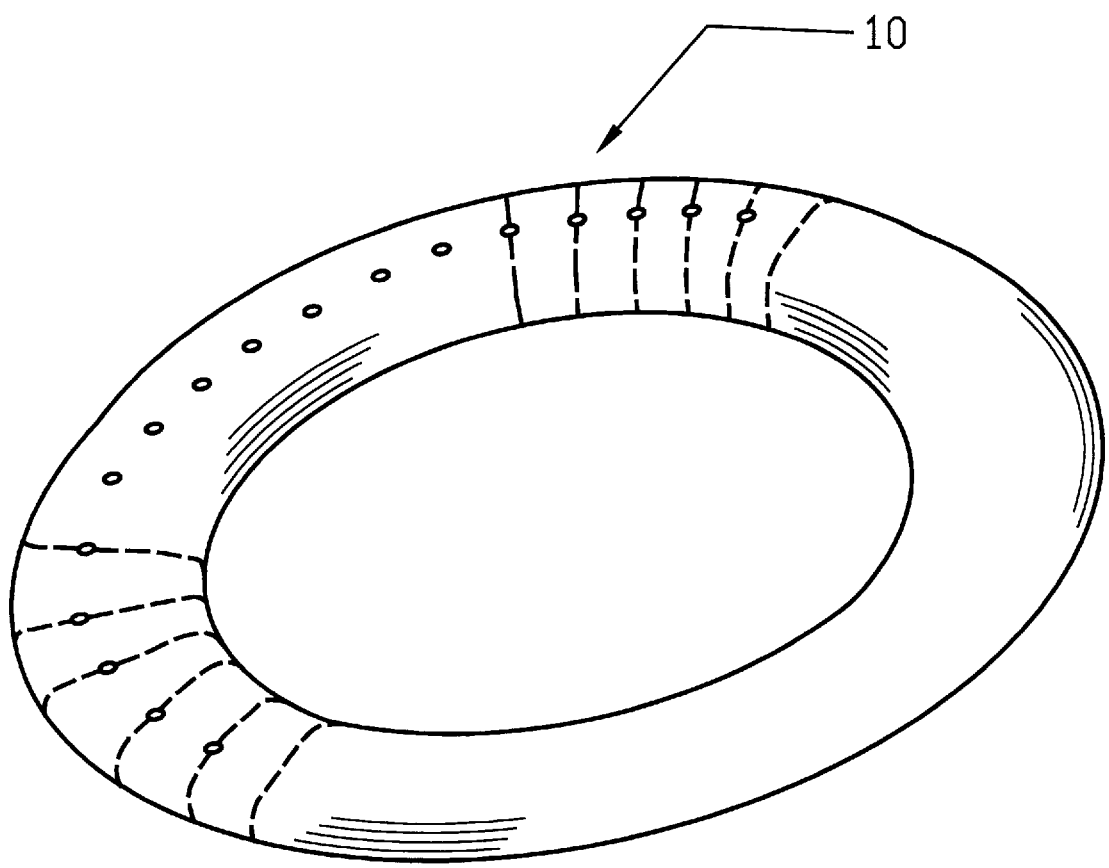
FIG. 5 is a perspective view of the device with a size adjustment means.
Figure 6:
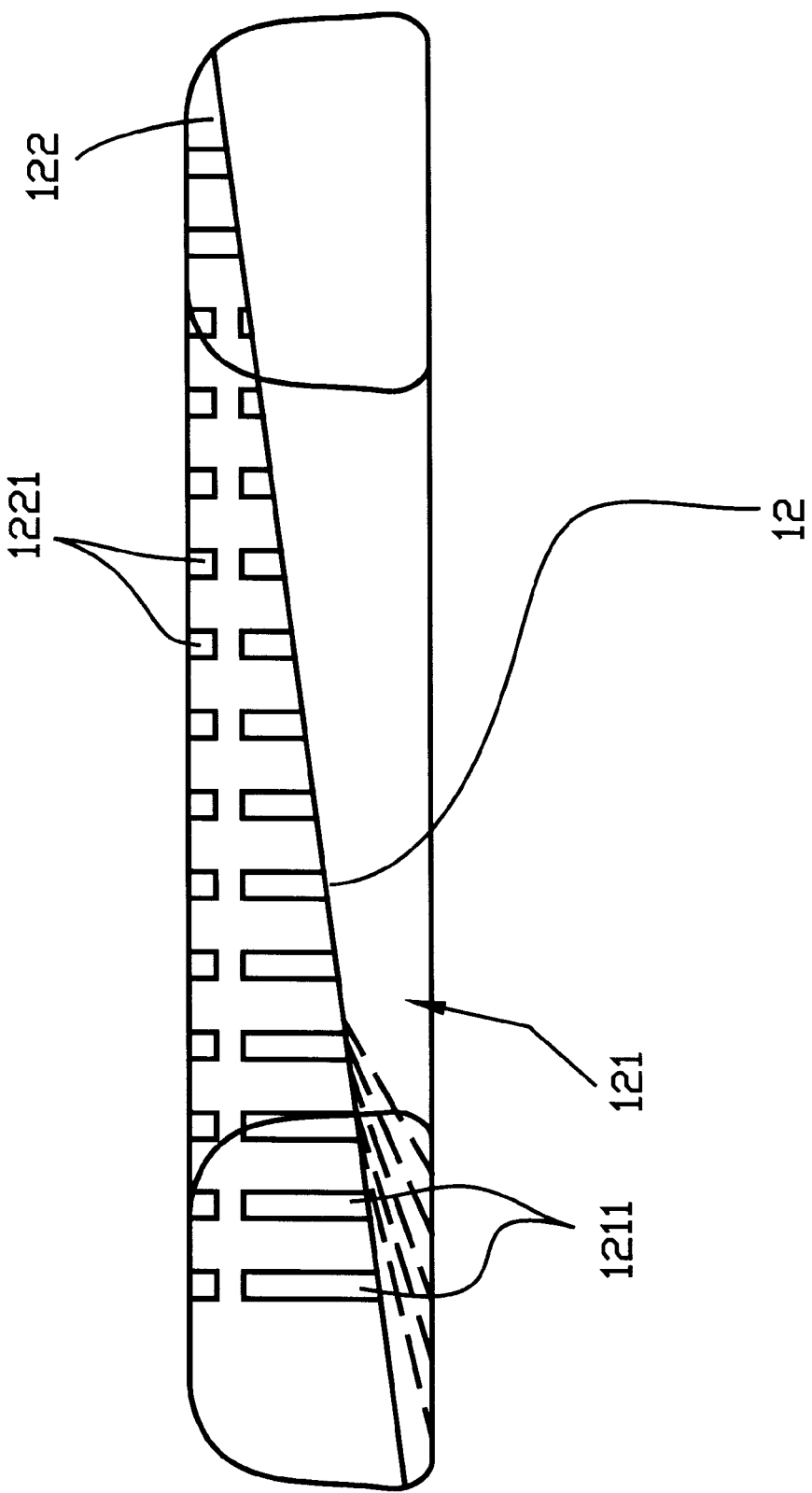
FIG. 6 is a cross section of the device with a size adjustment means.

A second size adjustment means is illustrated in FIGS. 5 and 6. In this instance, the device comprises a diagonal opening 12 that passes through the main body of the device, thus forming a first end 121 and a second end 122. The first end 121 includes a plurality of projections 1211. The second end includes a plurality of receiving apertures 1221. Size adjustment is accomplished by selectively inserting at least one of the projections 1211 into at least one of the apertures 1221.

Figure 7:
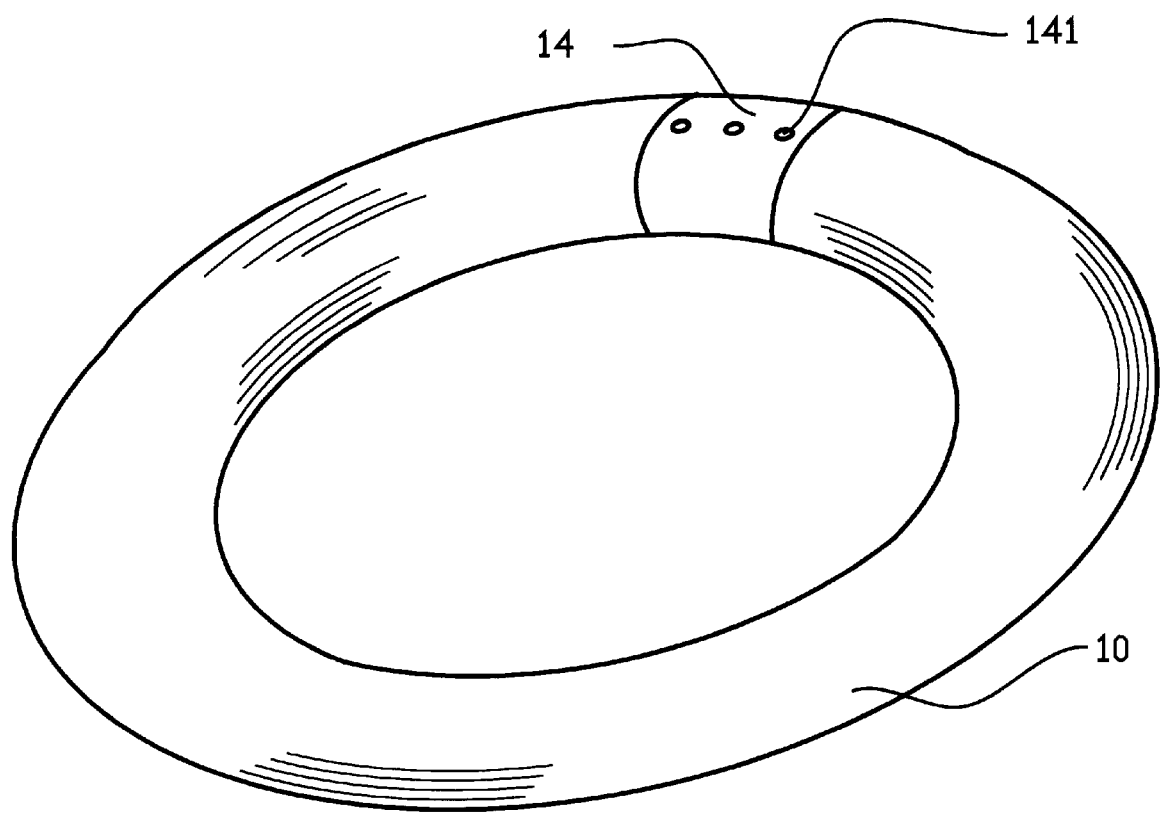
FIG. 7 is a perspective view of the device using an interior size adjustment means.
Figure 8:
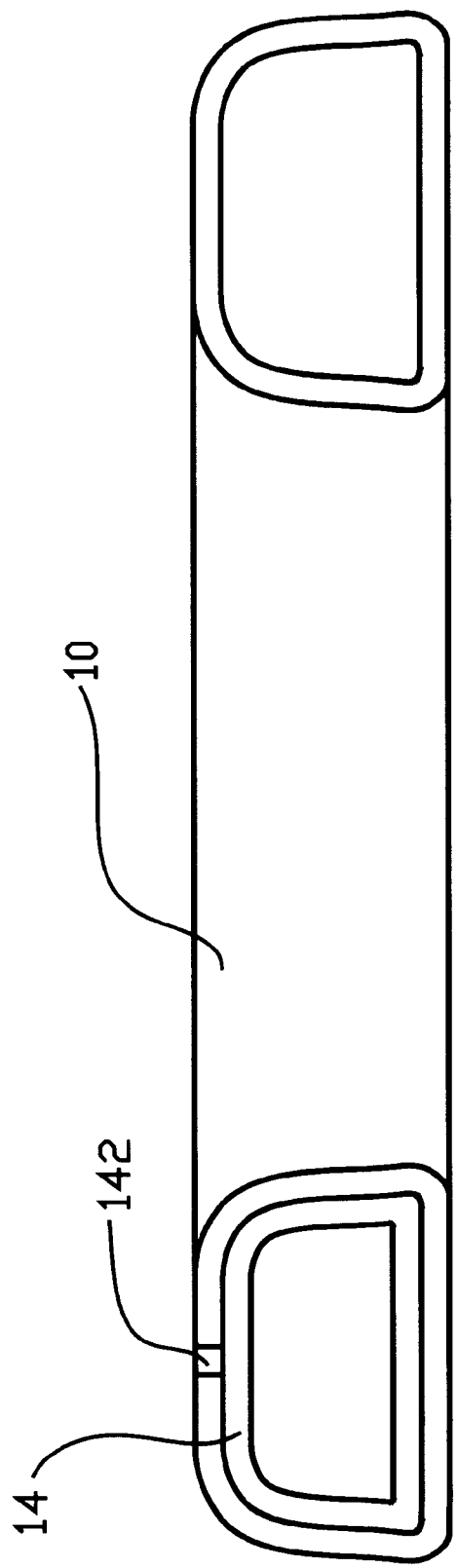
FIG. 8 is a cross section view of the device using an interior size adjustment means.
Figure 9:
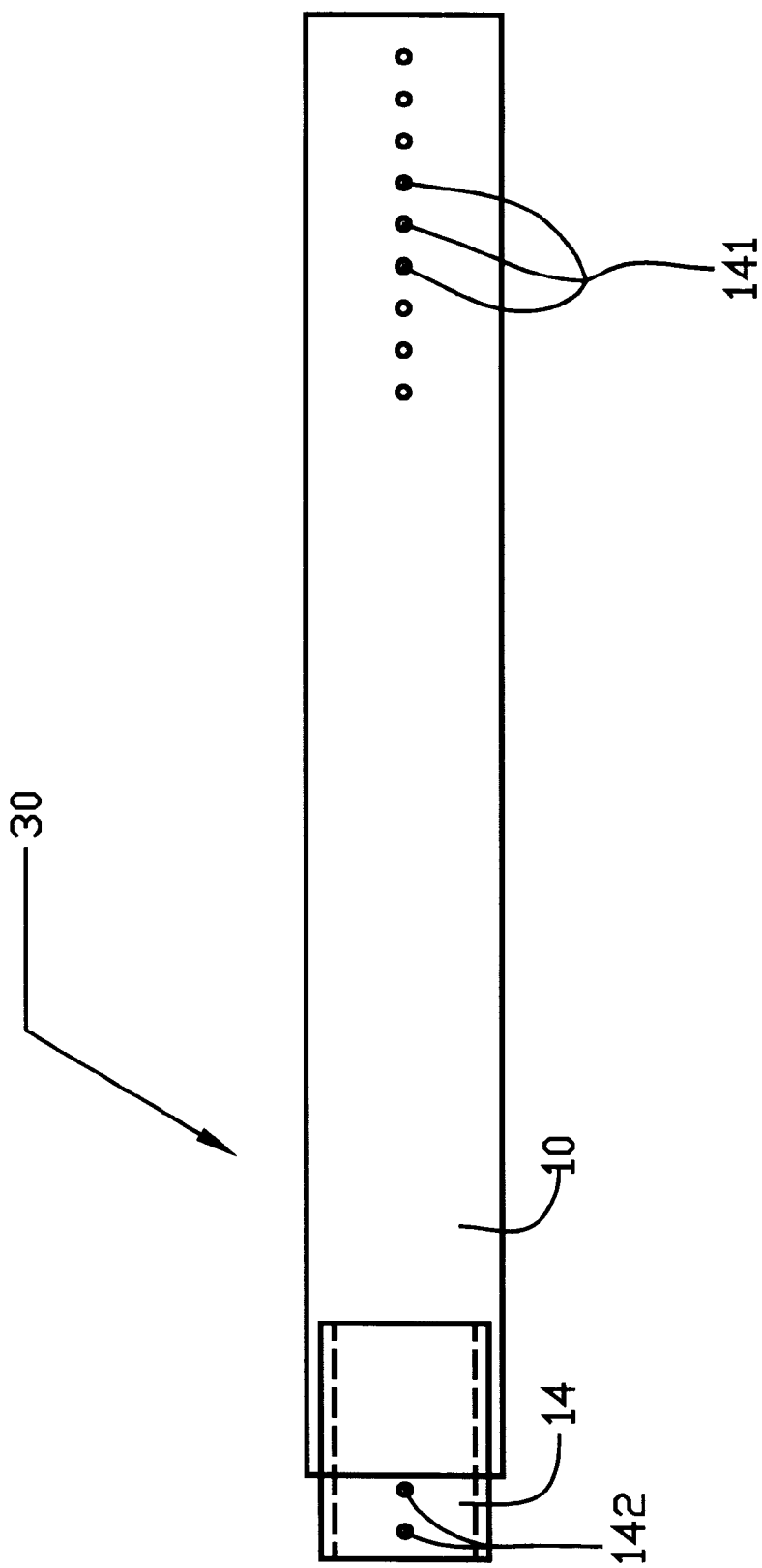
FIG. 9 is a top view of the device using an interior size adjustment means.
Figure 10:
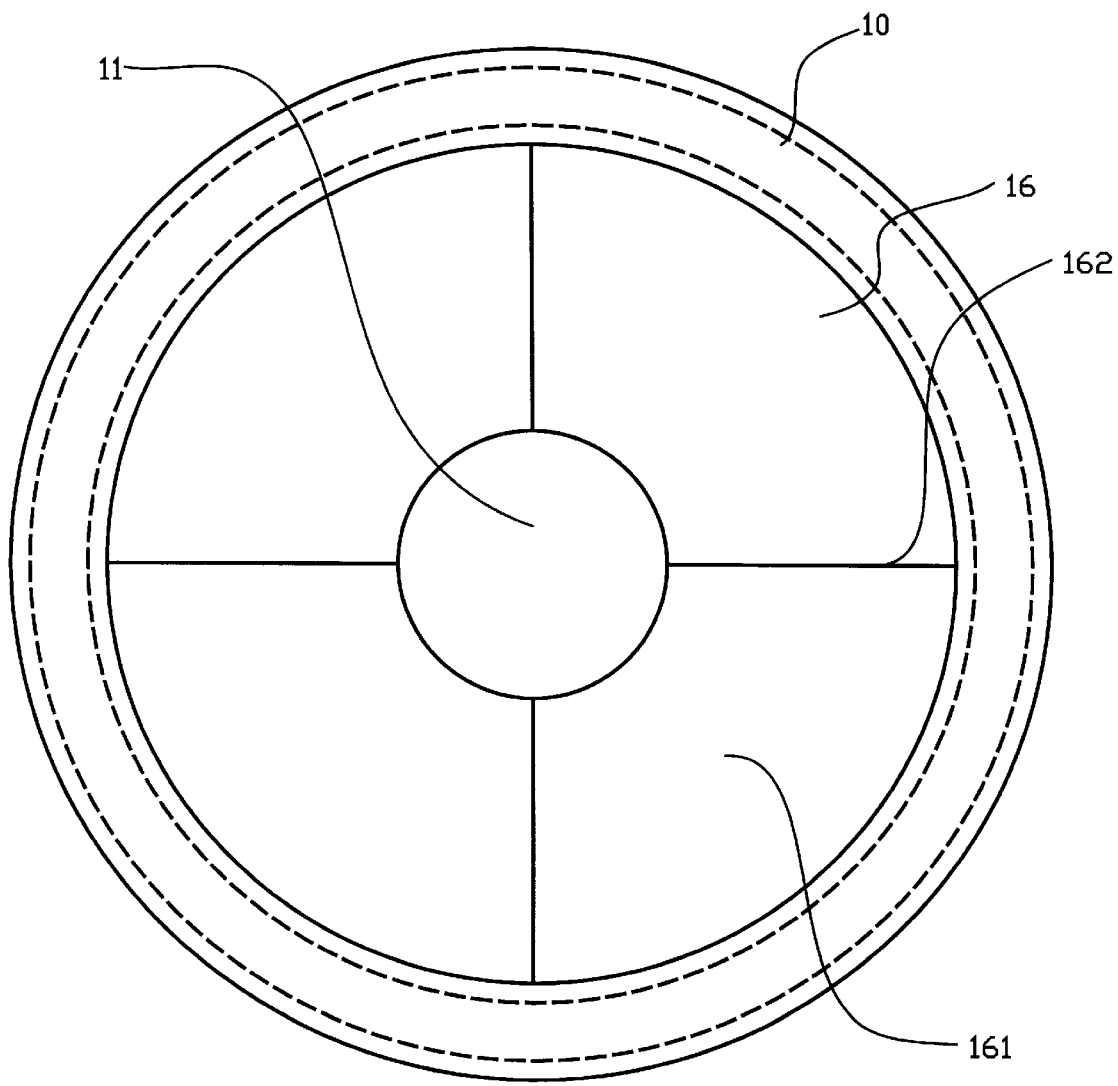
FIG. 10 is a top plan view of the device with a segmented membrane as the size adjustment means.
Figure 11:
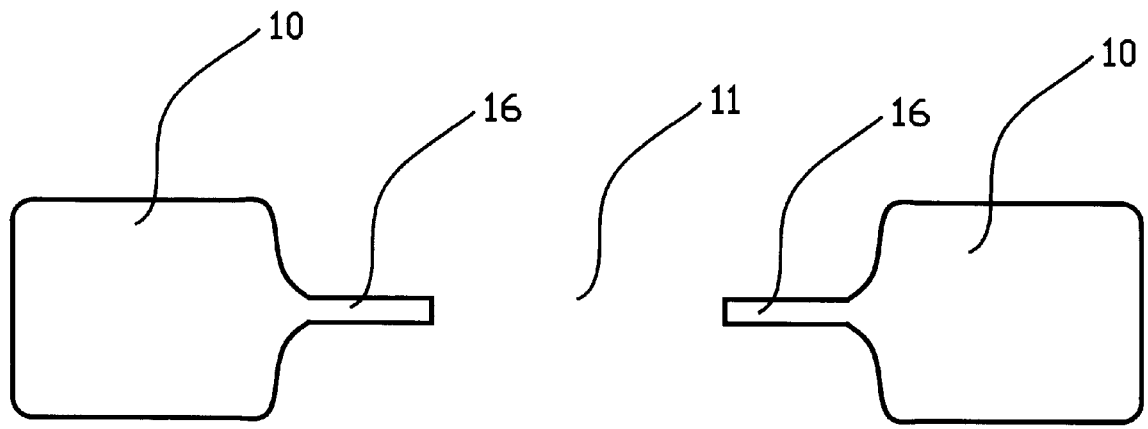
FIG. 11 is a cross section of the device with a segmented membrane as the size adjustment means.

FIGS. 7–9 illustrate the device employing an interior size adjustment means 14. When used with the interior size adjustment means 14, the main body 10 of the device will most likely be tubular, and will be formed by an extrusion process. The size adjustment means 14 will be secured in one end of the tubular main body 10.

The size adjustment means 14 includes one or more projections 141. In the preferred embodiment, these projections 141 extend upward from a top surface of the size adjustment means 14. The projections 141 are received in a series of corresponding holes 142 in the end of the main body 10 that does not have the size adjustment means secured therein. The size adjustment of the ring is accomplished by selecting which of the series of holes 142 receive the projections 141. The user inserts the size adjustment means 14 into the free end of the main body 10, where the projections 141 are received in the holes 142.

Still another means of accomplishing the size adjustment is by the use of a flexible membrane 16. The membrane 16 surrounds the central through hole 11, and an outer perimeter of the membrane 16 is affixed to the main body 10. The membrane 16 includes multiple slashes 162 so that the membrane 16 is divided into a plurality of segments 161. In the preferred embodiment, the number of segments is four. The division of the membrane 16 into multiple segments 161 increases the flexibility of the membrane while retaining its gripping characteristics.

Figure 12:
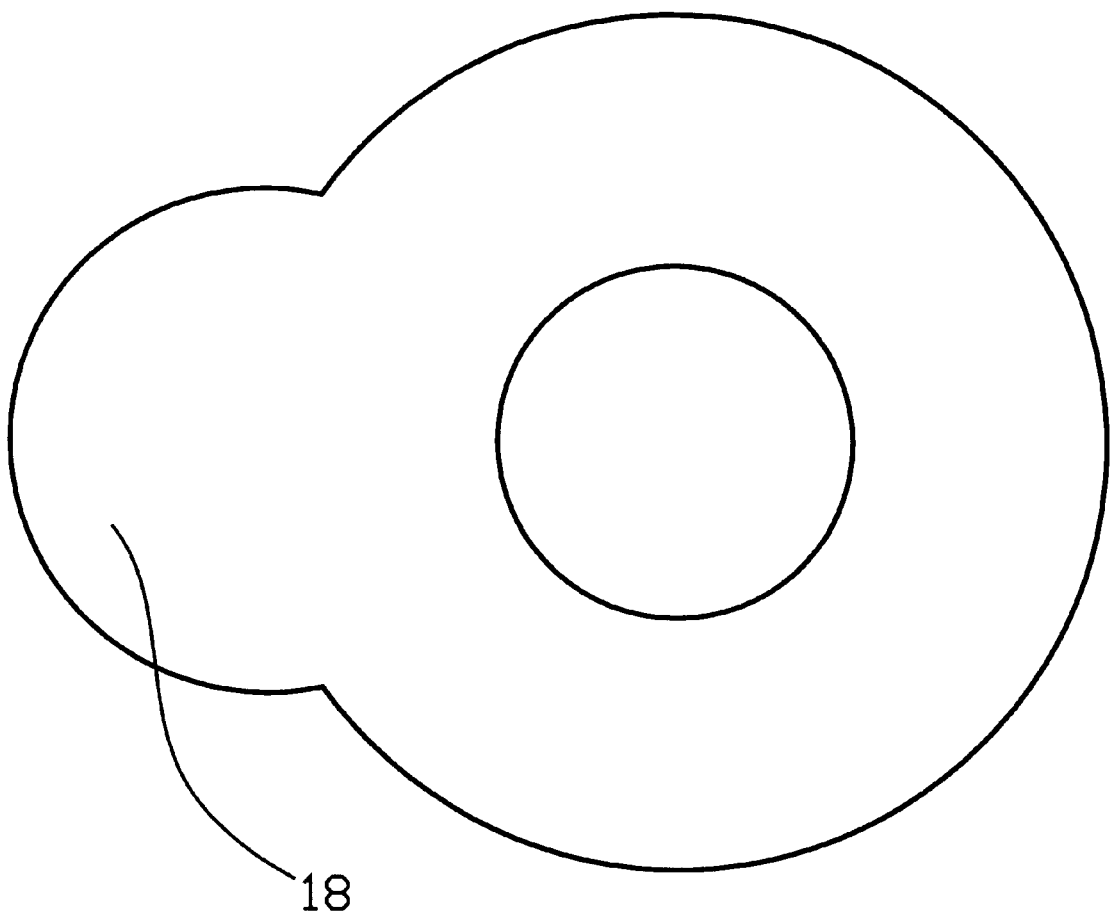
FIG. 12 is a top plan view of the device with a clitoral extension element.

The device may also include an extension means 18 to directly stimulate the female's clitoral region. A top view of the device with extension means 18 is shown in FIG. 12. The extension means 18 may be added to any embodiment of the device.

Figure 13:
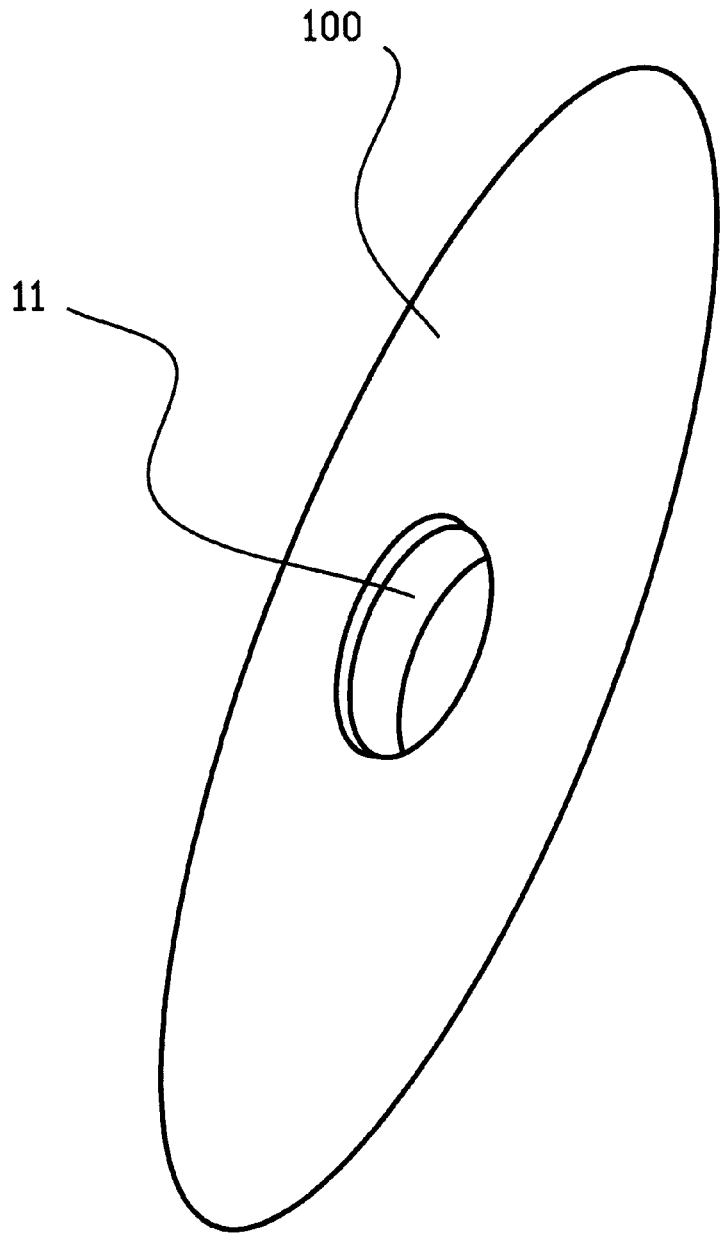
FIG. 13 shows the device with an oval shape.

FIG. 13 illustrates an alternative shape for the device. The ring 100 is oval in overall shape, so as to directly stimulate the clitoral region without the need for a protruding extension means 18. This increases the comfort of the device during use.

Figure 14:
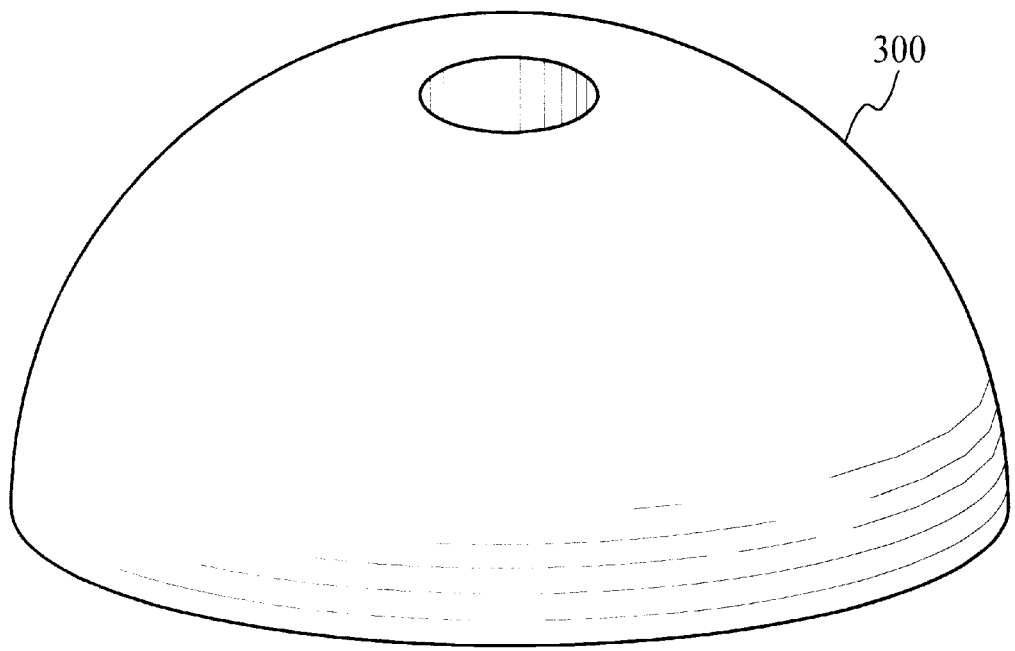
FIG. 14 is a perspective view of a penetrator element.
Figure 15:
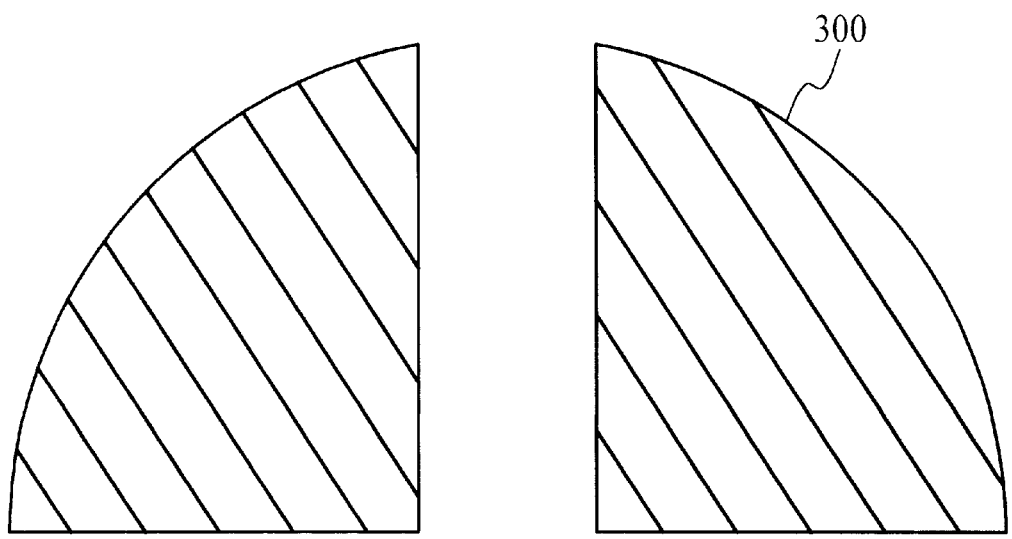
FIG. 15 shows a cross section of a penetrator element.

FIG. 14 shows an embodiment of the ring as a penetrator 300. The penetrator 300 may be used alone or in conjunction with any of the other rings. The penetrator 300 has continuously sloped walls so that it may be inserted into the female's vagina. The penetrator 300 also generally includes at least one of the above described size adjustment means.

The above disclosure is not intended as limiting. Those skilled in the art will readily observe that numerous modifications and alterations of the device may be made while retaining the teachings of the invention. Accordingly, the above disclosure should be construed as limited only by the restrictions of the appended claims.

I claim:

1. A sexual aid device comprising:

an outer ring and a plurality of inner rings, each of said inner rings has a different thickness, said outer ring interlocks with one of a plurality of inner rings to form a main body that includes a central through hole adapted to receive a user's penis, and a diameter of said central through hole is varied according to which one of said plurality of inner rings is chosen by the user, thereby ensuring that said device is secured in position while in use by the user.

2. The sexual aid device of claim 1 wherein:

said main body includes an extension means, said extension means is adapted to directly stimulate a clitoral region.

3. A sexual aid device comprising:

a main body, said main body includes a central through hole adapted to receive a user's penis, and a size adjustment means; wherein said size adjustment means serves to enlarge and reduce a diameter of said central through hole according to the user's requirements, said size adjustment means thereby ensuring that said device is secured in position while in use by the user, said size adjustment means comprises a diagonal slice that passes through said main body so as to form two tapered ends of said main body, a first tapered end of said main body includes projections thereon and a second tapered end of said main body includes apertures therein, said apertures selectively receive said projections so as to alter a position of said first tapered end relative to a position of said second tapered end such that said central through hole is enlarged and reduced.

4. The sexual aid device of claim 3 wherein:

said main body includes an extension means, said extension means is adapted to directly stimulate a clitoral region.

5. A sexual aid device comprising:

a main body, said main body includes a central through hole adapted to receive a user's penis, and a size adjustment means; wherein said size adjustment means serves to enlarge and reduce a diameter of said central through hole according to the user's requirements, said size adjustment means thereby ensuring that said device is secured in position while in use by the user, said size adjustment means comprises a vertical slice that passes through said main body so as to form two ends of said main body, a first end of said main body receives a first end of an elongated adjustment member in a first opening in said first end, and a second end of said main body includes a second opening to adjustably receive a second end of said elongated member therein, a plurality of projections are situated either on said second end of said elongated member or on an inner upper surface of said second opening, and a plurality of holes are located correspondingly in either an inner upper surface of said second opening or on said second end of said elongated member, so that said holes selectively receive said projections so as to alter a position of said first end of said main body relative to a position of said second end of said main body such that said central through hole is enlarged and reduced.

6. The sexual aid device of claim 5 wherein:

said main body includes an extension means, said extension means is adapted to directly stimulate a clitoral region.

7. A sexual aid device comprising:

a main body, said main body includes a central through hole that a main body, said main body includes a central through hole adapted to receive a user's penis, and a size adjustment means; wherein said size adjustment means serves to enlarge and reduce a diameter of said central through hole according to the user's requirements, said size adjustment means thereby ensuring that said device is secured in position while in use by the user, said size adjustment means comprises a flexible membrane that surrounds said central through hole, an outer perimeter of said membrane is affixed to an inner diameter of said main body, said membrane further includes a plurality of slashes so that said membrane is divided into a plurality of segments; wherein said segments are displaced when said device is placed on the user's penis, said segments thereby create a tension force that urges said segments against the user's penis, thereby securing said device in place.

8. The sexual aid device of claim 7 wherein:

said main body includes an extension means, said extension means is adapted to directly stimulate a clitoral region.

9. The sexual aid device of claim 7 wherein:

the number of said segments is four.

10. A sexual aid device comprising:

a main body that includes a central through hole adapted to receive a user's penis, a cross section of said main body decreases in width from a lower surface to an upper surface such that said main body is thin at said upper end relative to said lower end, such that said main body forms a penetrating element, and a size adjustment means; wherein said size adjustment means serves to enlarge and reduce a diameter of said central through hole according to the user's requirements, said size adjustment means thereby ensuring that said device is secured in position while in use by the user.

11. The sexual aid device of claim 10 wherein:

said device comprises an outer ring and a plurality of inner rings, each of said inner rings has a different thickness, said main body is formed by interlocking said outer ring with one of said inner rings, such that said diameter of said central through hole is enlarged and reduced according to the thickness of said inner ring chosen for use.

12. The sexual aid device of claim 10 wherein:

said size adjustment means comprises a diagonal slice that passes through said main body so as to form two tapered ends of said main body, a first tapered end of said main body includes projections thereon and a second tapered end of said main body includes apertures therein, said apertures selectively receive said projections so as to alter a position of said first tapered end relative to a position of said second tapered end such that said central through hole is enlarged and reduced.

13. The sexual aid device of claim 10 wherein:

said size adjustment means comprises a vertical slice that passes through said main body so as to form two ends of said main body, a first end of said main body receives a first end of an elongated adjustment member in a first opening in said first end of said main body, and a second end of said main body includes a second opening to adjustably receive a second end of said elongated adjustment member therein, a plurality of projections are situated either on said second end of said elongated adjustment member or on an inner upper surface of said second opening, and a plurality of holes are located correspondingly in either an inner upper surface of said second opening or on said second end of said elongated adjustment member, so that said holes selectively receive said projections so as to alter a position of said first end of said main body relative to a position of said second end of said main body such that said central through hole is enlarged and reduced.

14. The sexual aid device of claim 10 wherein:

said size adjustment means comprises a flexible membrane that surrounds said central through hole, an outer perimeter of said membrane is affixed to an inner diameter of said main body, said membrane further includes a plurality of slashes so that said membrane is divided into a plurality of segments; wherein said segments are displaced when said device is placed on the user's penis, said segments thereby create a tension force that urges said segments against the user's penis, thereby securing said device in place.

15. The sexual aid device of claim 14 wherein:

the number of said segments is four.

16. The sexual aid device of claim 10 wherein:

said main body includes an extension means, said extension means is adapted to directly stimulate a clitoral region.

* * * * *